(12) United States Patent
Latta

(10) Patent No.: US 11,690,916 B2
(45) Date of Patent: ***Jul. 4, 2023

(54) DERMAL SKIN PROTECTANT AND CARRIER

(71) Applicant: Inspired Material Solutions, LLC, Omaha, NE (US)

(72) Inventor: Mark A. Latta, Omaha, NE (US)

(73) Assignee: Inspired Material Solutions, LLC, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/303,915

(22) Filed: Jun. 10, 2021

(65) Prior Publication Data

US 2021/0290766 A1    Sep. 23, 2021

Related U.S. Application Data

(63) Continuation of application No. 16/674,895, filed on Nov. 5, 2019, now Pat. No. 11,071,786.

(60) Provisional application No. 62/755,719, filed on Nov. 5, 2018, provisional application No. 62/846,763, filed on May 13, 2019.

(51) Int. Cl.
| | | |
|---|---|---|
| A61K 47/34 | (2017.01) | |
| A61Q 17/00 | (2006.01) | |
| A61K 31/4425 | (2006.01) | |
| A61K 31/7048 | (2006.01) | |
| A61K 33/38 | (2006.01) | |
| A61K 31/635 | (2006.01) | |
| A61K 31/4174 | (2006.01) | |
| A61K 31/245 | (2006.01) | |
| A61K 38/12 | (2006.01) | |
| A61K 31/7036 | (2006.01) | |
| A61K 31/573 | (2006.01) | |
| A61K 31/195 | (2006.01) | |
| A61K 38/36 | (2006.01) | |
| A61K 38/48 | (2006.01) | |
| A61K 31/60 | (2006.01) | |
| A61K 31/5375 | (2006.01) | |
| A61K 31/352 | (2006.01) | |
| A61K 31/138 | (2006.01) | |
| A61K 8/92 | (2006.01) | |
| A61K 8/27 | (2006.01) | |
| A61Q 3/00 | (2006.01) | |
| A61K 31/14 | (2006.01) | |

(52) U.S. Cl.
CPC ............ *A61K 47/34* (2013.01); *A61K 8/27* (2013.01); *A61K 8/922* (2013.01); *A61K 31/138* (2013.01); *A61K 31/14* (2013.01); *A61K 31/195* (2013.01); *A61K 31/245* (2013.01); *A61K 31/352* (2013.01); *A61K 31/4174* (2013.01); *A61K 31/4425* (2013.01); *A61K 31/5375* (2013.01); *A61K 31/573* (2013.01); *A61K 31/60* (2013.01); *A61K 31/635* (2013.01); *A61K 31/7036* (2013.01); *A61K 31/7048* (2013.01); *A61K 33/38* (2013.01); *A61K 38/12* (2013.01); *A61K 38/363* (2013.01); *A61K 38/4833* (2013.01); *A61Q 3/00* (2013.01); *A61Q 17/00* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 5,393,745 A | 2/1995 | Schmidt et al. | |
| 5,651,959 A | 7/1997 | Hill et al. | |
| 7,264,882 B2 | 9/2007 | Engelbrecht | |
| 7,858,570 B2 | 12/2010 | Hare | |
| 8,603,550 B1 * | 12/2013 | Fusco ................. | A61K 8/9789 424/725 |
| 9,226,890 B1 | 1/2016 | Lamberty et al. | |
| 9,968,101 B2 | 5/2018 | Modak et al. | |
| 10,028,919 B2 | 7/2018 | Kaufman | |
| 2004/0033205 A1 | 2/2004 | Date et al. | |
| 2004/0167479 A1 | 8/2004 | Warren et al. | |
| 2008/0107742 A1* | 5/2008 | Hare ................... | A61K 31/125 424/489 |
| 2010/0047195 A1* | 2/2010 | Elbaum ................. | A61K 31/56 424/59 |
| 2012/0237464 A1 | 9/2012 | Ahn et al. | |
| 2014/0105941 A1 | 4/2014 | Mchale et al. | |
| 2015/0366786 A1 | 12/2015 | Huo et al. | |
| 2016/0106659 A1 | 4/2016 | Lamberty et al. | |
| 2017/0281520 A1* | 10/2017 | El-Khouri ............. | A61K 8/891 |
| 2018/0207213 A1* | 7/2018 | Mcelvany ............. | A61K 8/922 |
| 2018/0280282 A1 | 10/2018 | Mcconaughy et al. | |

FOREIGN PATENT DOCUMENTS

| | | |
|---|---|---|
| CN | 104814886 A | 8/2015 |
| WO | WO/2001/001940 A1 | 1/2001 |
| WO | WO/2014/059143 A1 | 4/2014 |
| WO | WO/2017/173267 A1 | 10/2017 |
| WO | WO/2018/075018 A1 | 4/2018 |
| WO | WO/2018/165078 A1 | 9/2018 |

OTHER PUBLICATIONS

International Search Report issued in International Application No. PCT/US2019/059783 dated Jan. 27, 2020.
"Polydimethylsiloxane", Wikipedia, Oct. 12, 2018, https://en.wikipedia.org/w/index.php?title=Polydimethylsiloxane&oldid=863655868.

* cited by examiner

*Primary Examiner* — Danah Al-Awadi
(74) *Attorney, Agent, or Firm* — Vos-IP, LLC

(57) ABSTRACT

A dermal skin protectant and carrier comprising a combination of two different viscosity dimethicone components, wherein the difference between the two different viscosity dimethicone components is about 2.0 million cP or greater; and comprising at least one active ingredient.

22 Claims, 4 Drawing Sheets

DERMAL SKIN PROTECTANT AND CARRIER

CROSS-REFERENCE TO RELATED APPLICATIONS

This application is a continuation of U.S. patent application Ser. No. 16/674,895 filed on Nov. 5, 2019, which claims the benefit of U.S. Provisional Patent Application No. 62/755,719 filed on Nov. 5, 2018, with the United States Patent and Trademark Office, and claims the benefit of U.S. Patent Application No. 62/846,763 filed on May 13, 2019, with the United States Patent and Trademark Office, the contents of each of which are incorporated herein by reference in their entirety.

FIELD OF INVENTION

The present invention is generally related to topically applied skin protectant materials, specifically dermal or nail skin protectant materials which also function as a carrier of excipients and other therapeutic compounds, suitable for topical administration to a skin surface for protecting skin and for providing a carrier for an additive or therapeutic to the skin surface. The dermal skin protectant material, comprising at least two different viscosity dimethicone components and at least one excipient for application to the skin surface.

BACKGROUND OF THE INVENTION

The dermal layer or skin is the first line of defense against the outside world. Accordingly, the skin is often the element that faces the greatest challenges from environmental hazards. One of the most common afflictions of the skin include cuts, bruises, rashes, fungal infections, bacterial infections, viral infections, and other irregularities. While nails and hair covering the skin provide some protection, in certain instances additional protection is warranted.

Skin protectant materials typically seek to create a barrier on the skin, thereby allowing the body to heal the skin, without further damage. For example, when a person has a cut, the application of a bandage protects the healing tissues with a clean protective covering material and, many of these bandages include wound closing or healing promoting compounds, or antibacterial materials or both. Accordingly, the bandage provides physical protection as well as adding compounds that promote healing of the underlying damaged tissues.

Physical bandages, however, can further irritate the skin with their adhesive materials, or in other cases, they simply cause irritation to the wound itself. Accordingly, there are instances where bandages are wrapped, instead of adhered, or where the wound is simply left open to prevent further damage.

Furthermore, most bandages contain a limited set of compounds on the skin facing surface of the bandage for contact with a wound. There are a number of reasons why this limitation exists, but to date, bandages that contain therapeutic materials are not in wide use.

Herein, the inventors have identified new skin protectant and topical dermal applied materials as well as methods of manufacturing the same that provide new and useful approaches towards skin and nail protection and application of therapeutics through dermal contact. These materials can be epicutaneously applied or provided within a bandage and applied to or over the skin as a cream, paste, foam, gel, liquid, paint, polish, or wherein the materials are embedded within a bandage.

SUMMARY OF THE INVENTION

The embodiments of the present disclosure detail a new and useful dermal applied material comprising a first and a second dimethicone-based products, which, when combined generate a unique material for dermal application. In preferred embodiments herein, at least one therapeutic can be advantageously combined into the material wherein the material is epicutaneously applied, wherein the therapeutic is transdermally transferred to the patient.

In a preferred embodiment, a dermal skin protectant and carrier comprising between 25-99% of a 12,500 cP dimethicone and between 1% and 50% of a 2.5 million cP dimethicone; and at least one therapeutic mixed therein.

A dermal skin protectant and carrier comprising between 25-99% of a 1,000 cP dimethicone and between 1% and 50% of a 2.5 million cP dimethicone; and at least one therapeutic mixed therein.

In a preferred embodiment, the skin protectant and carrier having a first and second dimethicone products, said first and second dimethicone products having a different at least 2.0 million cP differences in viscosity, and preferably a difference of about 2.5 million cP. In preferred embodiments, the difference is 2.5 million cP ±1%, 2%, 3%, 5%, 10%, or any number within that range.

In a preferred embodiment, a dermal skin protectant and carrier comprises a first and second dimethicone, said first dimethicone having a viscosity between 1,000 and 25,000 cP, and a second dimethicone having a viscosity of between 2.0 million cP and 3.0 million cP; and at least one therapeutic admixed therein.

A dermal skin protectant and carrier comprising two dimethicone polymers, and a therapeutic agent; a first dimethicone polymer having a formula of $Me_3$-O—$[SiMe_2]n$-$Me_3$ wherein n is a number of repeating units, having a viscosity of between about 1,000 and 25,000 cP, and a second dimethicone polymer having a formula wherein n is larger than the first dimethicone polymer, and having a thicker viscosity of between about 2.0 million cP and 3.0 million cP; with the first dimethicone polymer comprising between 10 and 99 percent of the total mass of the formulation and said second dimethicone polymer comprising between 1 and 90 percent of the total mass of the formulation.

A dermal skin protectant and carrier comprising two dimethicone polymers, and a therapeutic agent; a first dimethicone polymer having a formula of $Me_3$-O—$[SiMe_2]n$-$Me_3$ with "n" repeating units, and a second dimethicone polymer having a greater viscosity and more "n" repeating units than the first dimethicone polymer; with the first dimethicone polymer in a ratio with the second dimethicone polymer of between 100:1 to 1:10. Preferably the ratio is between about 75:1 to about 1:2, or about 50:1 to about 1:1.

A method of formulating a dermal skin protectant and carrier comprising: Mixing a first quantity of a first dimethicone component and at least one excipient or active agent in a centripetal mixer; mixing the first dimethicone component and at least one excipient or active agent for 10 minutes at 3,000 RPM; adding to the mixed material, a portion of a second dimethicone component having a viscosity of more than 2.0 million cP greater than the first dimethicone, wherein the second dimethicone is mixed in several increments; wherein each increment takes an equal portion of the original amount of the second dimethicone which is admixed into the mixed material at 3,000 RPM for 5 minutes before adding a further incremental portion of the second dimethicone until all of the second dimethicone is admixed into the mixture. In preferred embodiments, the second dimethicone is split into 2, 3, 4, 5, or 10 increments for mixture into the first mixture.

In preferred embodiments, the combination of a first dimethicone and a second dimethicone are combined with an active ingredient. In certain embodiments, the active ingredient is provided in a dose amount that is suitable for over-the-counter sales. In certain embodiments, the dose or active ingredient is required for sale under prescription.

In certain embodiments, it is preferable to identify different release profiles for different purposes. Accordingly, a dermal skin protectant and carrier may comprise a 1:10 ratio of a low viscosity to a high viscosity dimethicone, to a 100:1 ratio of low viscosity to high viscosity dimethicone and all ratios in between. The different concentrations allow for different physical properties, including different physical characteristics (solid or gel-like) as well as different rates of release.

In a preferred embodiment, the material is a wound care material, comprising a first and second dimethicone, said first dimethicone having a viscosity between 1,000 and 25,000 cP, and a second dimethicone having a viscosity of between 2.0 million cP and 3.0 million cP, and at least one therapeutic admixed therein, wherein said therapeutic is selected from the group consisting of: antibiotic materials, sulfur compounds, skin healing compounds, bone growth promoting compounds, antimicrobial agents, topical anesthetic, antifungal, $CoQ_{10}$, vitamin D, chlorhexidine, FDA monographed compounds identified at the Web address https://www.fda.gov/downloads/AboutFDA/CentersOffices/CDER/UCM135688.pdf, chitosan, hemostatic materials, anti-inflammatory, topical steroid, anti-inflammatory compounds, hemp-based extracts including cannabinoids and terpenes including but not limited to THC and CBD, silver nitrate, essential oils, skin protectant, pain relief or blocking agents, zinc oxide, small molecules, nitroglycerin, nicotine, hormones, or combinations thereof.

In certain preferred embodiments, the material is indicated for vaginal application, wherein the material can be provided as a lubricant, or wherein admixed therein is an antifungal, including but not limited to clotrimazole, econazole, miconazole, terbinafine, fluconazole, ketoconazole, mophotericin, nystatin, sporanox, difulcan, terazol, intraconazole, mycostatin, boric acid, tioconazole, or another known antifungal (including those listed below), whether natural or synthetic, a derivative or prodrug thereof, or combinations thereof. In certain preferred embodiments, the antifungal is suitable for any skin tissues and may include the above antifungals or one of the following: undecylenic acid, tolnaftate, imidazole, luliconazole, tavaborole, allylamine, amorolfine, oxiconazole, gluconazole, ciclotirox, naftifine, amphotericin B, sulconazole, butenafine, sertaconazole, efinacanazole, and other known antifungal compounds natural or synthetic, or combinations thereof. In certain embodiments, the material further comprises at least one skin protectant therapeutic. In certain embodiments, the material further comprises at least one deodorant or antiperspirant material. In certain preferred embodiments, the material comprises at least one anesthetic component.

In certain preferred embodiments, a material for application to the nasal mucosa and carrier comprises a first and second dimethicone, said first dimethicone having a viscosity between 1,000 and 25,000 cP, and a second dimethicone having a viscosity of between 2.0 million cP and 3.0 million cP; and at least one therapeutic admixed therein selected from a skin protectant, a steroid, an anti-inflammatory, an antihistamine, or a suitable therapeutic for uptake within the nasal mucosa.

In certain preferred embodiments, the material is applied to a skin surface, or to a nail or hair material, wherein the adherent properties of the material provide for a barrier layer on the underlying surface and also allow for a therapeutic to be released from the material to the underlying skin, nail, or hair.

In certain preferred embodiments, for any of the topical applications the material comprises an essential oil.

In certain preferred embodiments, for any of the topical applications provided above, the material may further comprise an antimicrobial compound. In certain other embodiments, the material may further comprise an odor fighting material, or odor masking material.

In certain preferred embodiments, the material is defined as a skin protectant material; which is advantageously combined with one or more excipients to form both a barrier and to function as a carrier for release of materials for skin protectant for treatment of rashes, as an antimicrobial, for pain relief, with zinc oxide, as a carrier for small molecules, as a carrier for THC/CBD, as a carrier for nitroglycerin and may further include but is not limited to: testosterone; nicotine, hormones, antinausea agent, estrogen replacement, fentanyl (or other pain relief), transdermal scopaline, hypertensine, MAOI antidepressant, ADHD, vitamin $B_{12}$, 5-THP, retin-A, or combinations thereof.

In certain preferred embodiments, the material is a skin protectant for the lips. In a preferred embodiment, the material for lip care further comprises an excipient selected from the group consisting of: a moisturizer, flavor, pigment, essential oils, zinc oxide, a wetting agent to create shine for lip gloss or lipstick, and combinations thereof.

In a preferred embodiment, a dimethicone-based dermal skin protectant and carrier comprising a first dimethicone material having a viscosity of between about 1,000 cP and 25,000 cP, and a second dimethicone material having a viscosity of between about 2.0 million and 3.0 million cP; and at least one active agent.

In a further embodiment, a dimethicone-based skin protectant of any of the above embodiments, wherein the at least one active agent is selected from the group consisting of: antibiotic materials, antimicrobial antifungal; FDA monographed compounds identified at https://www.fda.gov/downloads/AboutFDA/CentersOffices/CDER/UCM135688.pdf; hemostatic materials; anti-inflammatory; topical steroid; THC/CBD; essential oils, skin protectant, pain relief, zinc oxide, hormones, and combinations thereof.

In certain preferred embodiments, the material is a hair and scalp treatment material, for treating fungal, yeast, mold, bacterial, or viral infections of the hair, hair follicle and the scalp, or dermal tissues.

In certain preferred embodiments, the material is a nail treatment, for topical application to a nail surface. In preferred embodiments, the nail application is applied as a gel, paste, foam, solid, or liquid, and/or may further comprise hardening agents to allow formation as a nail polish.

A composition comprising a first dimethicone material having a viscosity of between about 1,000 cP and 25,000 cP, and a second dimethicone material having a viscosity of between about 2.0 million and 3.0 million cP; and at least one active agent.

In one embodiment, the composition is a dermal skin protectant and carrier wherein the at least one active agent is selected from the group consisting of: an antimicrobial agent, an anesthetic agent, a hemostatic agent, an anti-inflammatory agent, a hemp-based extract, a deodorant, a pain relief agent, a UV protection agent, and combinations thereof. In one embodiment, the composition wherein two or more active agents are combined together in the dermal skin protectant and carrier.

In one embodiment, the composition wherein the ratio of the first dimethicone to the second dimethicone is between 100:1 and 1:10. In one embodiment, the composition wherein the ratio of the first dimethicone to the second dimethicone is between 50:1 and 1:5. In one embodiment, the composition wherein the ratio of the first dimethicone to the second dimethicone is between 40:1 and 1:2. In one embodiment, the composition wherein the concentration of the at least one active agent is between 0.5 and 10%.

In one embodiment, the composition further comprising a second active agent.

In one embodiment, the composition further comprising at least one antifungal, antiviral, or antibacterial agent.

In one embodiment, the composition further comprising at least one topical anesthetic agent.

In one embodiment, the composition further comprising at least one deodorant.

In one embodiment, the composition further comprising at least one essential oil. In one embodiment, the composition further comprising an extract of a hemp plant.

In one embodiment, the composition further comprising at least one antimicrobial agent. In a preferred embodiment, the antimicrobial agent is an antibacterial, an antifungal, or an antiviral specific agent. In a further preferred embodiment the antimicrobial agent is benzalkonium chloride or cetylpyridinium chloride.

In a further embodiment, a method of formulating a skin protectant of the above embodiments, comprising placing the entirety of a first dimethicone component into a mixing container and adding into it an amount of a therapeutic agent; mixing the two components at 3,000 RPM for about 10 minutes in a centripetal mixer, after mixing for 10 minutes, the second dimethicone was added, with one fifth of the total concentration of the second dimethicone added in equal parts, followed by mixing at 3,000 RPM for five minute increments until all of the second dimethicone is added and mixed for five minutes.

In one embodiment, the method further comprising adding at least one active agent with the first dimethicone and therapeutic agent before mixing the components.

In one embodiment, the method further comprising admixing a first and second therapeutic agent, and any excipients to the first dimethicone before admixing the second dimethicone.

In a further embodiment, a dimethicone-based antifungal delivery composition comprising: a first dimethicone having a viscosity between 1,000 cP and 25,000 cP, and a second dimethicone having a viscosity between 2.0 million cP and 3.0 million cP, and an effective amount of an antifungal composition. In a preferred embodiment, wherein the antifungal composition is selected from the group consisting of: clotrimazole, econazole, miconazole, terbinafine, fluconazole, ketoconazole, mophotericin, nystatin, sporanox, difulcan, terazol, intraconazole, mycostatin, boric acid, tioconazole, undecylenic acid, tolnaftate, imidazole, luliconazole, tavaborole, allylamine, amorolfine, oxiconazole, gluconazole, ciclotirox, naftifine, amphotericin B, sulconazole, butenafine, sertaconazole, efinaconazole, a derivative or prodrug thereof, and combinations thereof. In one embodiment, wherein the antifungal composition is Nystatin. In one embodiment, wherein the antifungal composition further comprises *Aloe vera*. In one embodiment, wherein the antifungal composition is clotrimazole. In one embodiment, wherein the antifungal composition is applied to a skin surface, a nail surface, or a hair.

In a further embodiment, a dimethicone-based antibacterial delivery composition comprising: a first dimethicone having a viscosity between 1,000 cP and 25,000 cP, and a second dimethicone having a viscosity between 2.0 million cP and 3.0 million cP, and an effective amount of an antibacterial composition. In one embodiment, wherein the antifungal composition is applied to a skin surface, a nail surface, or hair.

In a further embodiment, a dimethicone-based skin composition for treating burned skin comprising a first dimethicone having a viscosity between 1,000 cP and 25,000 cP, and a second dimethicone having a viscosity between 2.0 million cP and 3.0 million cP, and an effective amount of a skin care material and an effective amount of a topical anesthetic. In one embodiment, the skin care material is selected from the group consisting of: chitosan, sulfadiazine, silver sulfadiazine, silver nitrate, silver nanoparticles, and combinations thereof. In one embodiment, wherein the topical anesthetic is selected from the group consisting of benzocaine, butamben, tetracaine, benzyl alcohol, capsaicin, dibucaine, diclofenac, dyclonine, ethyl chloride, hexylresorcinol, lidocaine, prilocaine, methyl salicylate, menthol, pramoxine, proparacaine, trolamine, and combinations thereof.

In a further embodiment, a dimethicone-based composition for topical wound healing comprising: first dimethicone having a viscosity between 1,000 cP and 25,000 cP, and a second dimethicone having a viscosity between 2.0 million cP and 3.0 million cP, and an effective amount of a wound healing composition. In one embodiment, wherein said wound healing composition is selected from the group consisting of: bacitracin; neomycin; polymyxin B, epidermal growth factor, triamcinolone, and combinations thereof.

A dimethicone composition for hemostatic treatment comprising: a first dimethicone having a viscosity between 1,000 cP and 25,000 cP, and a second dimethicone having a viscosity between 2.0 million cP and 3.0 million cP, and an effective amount of a hemostatic composition. In one embodiment, the composition, wherein said hemostatic composition is selected from the group consisting of: tranexamic acid, chitosan, human fibrinogen, human thrombin, nonhuman fibrinogen or thrombin, synthetic fibrinogen or thrombin, keratin, aluminum chloride, ferric sulfate, ferric subsulfate, chitosan, kaolinate or other clays, and combinations thereof.

A dimethicone composition for treatment of acne comprising a first dimethicone having a viscosity between 1,000 cP and 25,000 cP, and a second dimethicone having a viscosity between 2.0 million cP and 3.0 million cP, and an effective amount of an active ingredient selected from the group consisting of: benzoyl peroxide, azelic acid, salicylic acid, retinoids combined with antibiotics including but not limited to tetracycline, clindamycin and erythromycin, and combinations thereof.

A dimethicone composition for treatment of hemorrhoids comprising a first dimethicone having a viscosity between 1,000 cP and 25,000 cP, and a second dimethicone having a viscosity between 2.0 million cP and 3.0 million cP, and an effective amount of an active ingredient selected from the group consisting of: phenylephrine hydrochloride, pramoxine HCl, corticosteroids, and combinations thereof.

A dimethicone composition for delivering hemp extracts to a dermal surface comprising: a first dimethicone having a viscosity between 1,000 cP and 25,000 cP, and a second dimethicone having a viscosity between 2.0 million cP and 3.0 million cP, and an effective amount of a hemp extract. In preferred embodiments the hemp extract comprising CBD, THC, terpenes, or combinations thereof.

A dimethicone composition for cannabinoid delivery system comprising a first dimethicone having a viscosity between 1,000 cP and 25,000 cP, and a second dimethicone having a viscosity between 2.0 million cP and 3.0 million cP; and at least one therapeutic mixed therein, wherein the therapeutic is a hemp-based extract. In a preferred embodiment, the first dimethicone comprises between 10-99% of the total weight of the composition, and wherein the second dimethicone comprises between 1 and 90% of the total weight of the composition. In preferred embodiments, wherein the hemp-based extract comprises a cannabinoid (including but not limited to THC or CBD) or a terpenoid.

A dimethicone composition for treatment of anti-inflammatory material comprising: a first dimethicone having a viscosity between 1,000 cP and 25,000 cP, and a second dimethicone having a viscosity between 2.0 million cP and 3.0 million cP, and an effective amount of an active ingredient selected from the group consisting of: diphenhydramine, a corticosteroid, or other anti-inflammatory compound, and combinations thereof.

A dimethicone composition for delivery of ferric subsulfate comprising a first dimethicone having a viscosity between 1,000 cP and 12,500 cP, and a second dimethicone having a viscosity between 2.0 million cP and 3.0 million cP, and an effective amount of a ferric subsulfate material. In one embodiment, wherein the ferric subsulfate material is Monsel's solution.

A dimethicone composition comprising a first dimethicone material having a first viscosity and a second dimethicone material having a second viscosity, wherein the difference between the first and second viscosity is at least 2.0 million cP; and further comprising at least one active agent admixed into the first and second dimethicone. In a preferred embodiment wherein the active agent is a therapeutic agent selected from the group consisting of: benzalkonium chloride, cetylpyridinium chloride, nystatin, sulfur compounds, colloidal silver compounds, ferric subsulfate, hemostatic agents including fibrinogen, thrombin, and chitin, mucositis treatments, sulfur compounds, antimicrobial, topical anesthetics, antifungal, $CoQ_{10}$, vitamin D, chlorhexidine, chitosan, hemostatic materials, anti-inflammatory, topical steroid, antihistamine, THC/CBD, silver nitrate, peppermint, cinnamon, wintergreen, chlorine, antifungal, skin protection, deodorant, anesthetic, steroid, essential oils, odor masking or preventing, skin protectant, antimicrobial and antibacterial, pain relief, zinc oxide, small molecules for therapeutic treatment of mammals, nitroglycerin, testosterone, nicotine, hormones, nausea treatment, estrogen replacement, opioid compounds, transdermal scopaline, hypertensine, MAOI antidepressant, ADHD, vitamin $B_{12}$, 5-THP, retin-A, and combinations thereof.

A method of manufacturing a dermal skin protectant and carrier comprising: a first dimethicone material having a viscosity of between about 1,000 cP and 25,000 cP, and a second dimethicone material having a viscosity of between about 2.0 million and 3.0 million cP; and at least one active agent; the method comprising: placing the first dimethicone component into a mixing container and adding into it an amount of the active agent and mixing the combination at 3,000 RPM for about 10 minutes in a centripetal mixer; after mixing the at least one active agent into the first dimethicone, adding the second dimethicone to the mixing chamber, with one fifth of the total concentration of the second dimethicone added in equal increments, followed by mixing at 3,000 RPM for five minute increments until all of the second dimethicone is added and mixed for five minutes.

In a preferred embodiment, a dimethicone-based delivery composition comprising: a first dimethicone having a viscosity between 1,000 cP and 25,000 cP, and a second dimethicone having a viscosity between 2.0 million cP and 3.0 million cP, and an effective amount of an active agent.

In a preferred embodiment, the dimethicone-based delivery composition wherein the active agent is an antifungal composition. In a preferred embodiment, the dimethicone-based delivery composition wherein the antifungal composition is selected from the group consisting of: clotrimazole, econazole, miconazole, terbinafine, fluconazole, ketoconazole, mophotericin, nystatin, sporanox, difulcan, terazol, intraconazole, mycostatin, boric acid, tioconazole, undecylenic acid, tolnaftate, imidazole, luliconazole, tavaborole, allylamine, amorolfine, oxiconazole, gluconazole, ciclotirox, naftifine, amphotericin B, sulconazole, butenafine, sertaconazole, efinacanazole, a derivative or prodrug thereof, and combinations thereof. In a preferred embodiment, the dimethicone-based delivery composition wherein the composition further comprises *Aloe vera*.

In a preferred embodiment, the dimethicone-based delivery composition wherein the active agent is a topical anesthetic. In a preferred embodiment, the dimethicone-based delivery composition wherein the active agent is a skin care material, and wherein the skin care material is selected from the group consisting of: chitosan, sulfadiazine, silver sulfadiazine, silver nitrate, silver nanoparticles, and combinations thereof. In a preferred embodiment, the dimethicone-based delivery composition wherein the topical anesthetic is selected from the group consisting of benzocaine, butamben, tetracaine, benzyl alcohol, capsaicin, dibucaine, diclofenac, dyclonine, ethyl chloride, hexylresorcinol, lidocaine, prilocaine, methyl salicylate, menthol, pramoxine, proparacaine, trolamine, and combinations thereof.

In a preferred embodiment, the dimethicone-based delivery composition wherein the active ingredient is a wound healing composition selected from the group consisting of: bacitracin; neomycin; polymyxin B, epidermal growth factor, triamcinolone, and combinations thereof. In a preferred embodiment, the dimethicone-based delivery composition wherein the active ingredient is a hemostatic composition selected from the group consisting of: tranexamic acid, chitosan, human fibrinogen, human thrombin, nonhuman fibrinogen or thrombin, synthetic fibrinogen or thrombin, keratin, or combinations thereof.

In a preferred embodiment, the dimethicone-based delivery composition, wherein the active ingredient is a ferric subsulfate material or Monsel's solution. In a preferred embodiment, the dimethicone-based delivery composition further comprising: an excipient, wherein said excipient is selected from the group consisting of: a moisturizer, flavor, pigment, essential oils, zinc oxide, a wetting agent, and combinations thereof.

In a preferred embodiment, the dimethicone-based delivery composition wherein the active ingredient is an acne treating agent selected from the group consisting of: benzoyl peroxide, azelic acid, salicylic acid, corticosteroids, retinoids, antibiotics, and combinations thereof.

In a preferred embodiment, the dimethicone-based delivery composition wherein the active agent is a hemorrhoid treating agent selected from the group consisting of phenylphrenie hydrochloride, pramoxine HCL, a corticosteroid, and combinations thereof.

In a preferred embodiment, the dimethicone-based delivery composition wherein the active agent is a hemp-based extract, wherein said hemp-based extract comprises at least one cannabinoid.

In a preferred embodiment, the dimethicone-based delivery composition wherein the active ingredient is an anti-inflammatory agent, and wherein said anti-inflammatory agent is selected from the group comprising diphemhydramine, corticosteroids, and combinations thereof.

In a preferred embodiment, the dimethicone-based delivery composition wherein the active ingredient is an antimicrobial agent and wherein said antimicrobial agent is selected from the group consisting of an antifungal, antibiotic, or antiviral composition.

In a preferred embodiment, the dimethicone-based delivery composition further comprising an excipient selected from the group consisting of: an oil, a fat, a wax, and combinations thereof.

Use of a dermal skin protectant and carrier of any of the provided embodiments, comprising applying the dermal skin protectant and carrier to a dermal surface.

DETAILED DESCRIPTION OF THE INVENTION

As used herein, the term "about" means within 10% of a stated number.

Here, described is a dermal skin protectant and carrier and protectant product that provides a carrier for an excipient for treatment of the affliction as well as a barrier material to provide skin protection.

Figure 1:
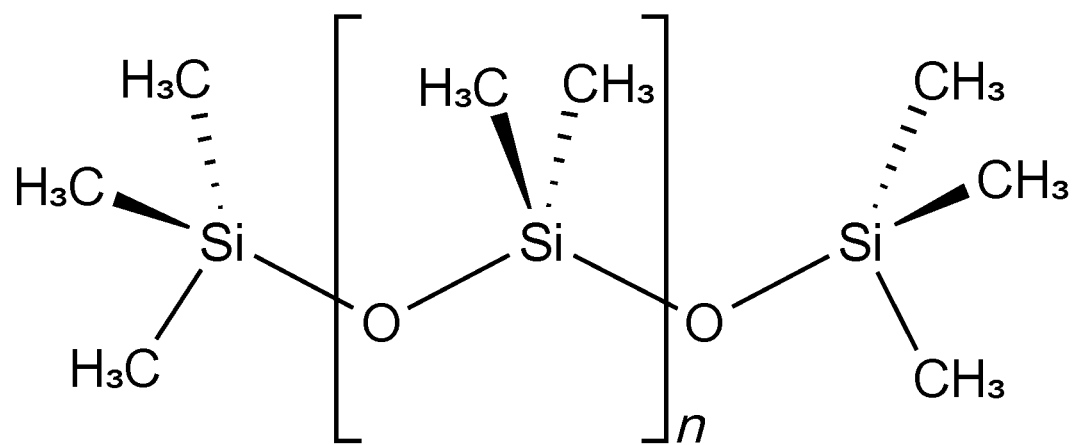
FIG. 1 depicts a figure of the formula of PDMS (Dimethicone) having n number of repeating siloxane units.

In preferred embodiments, a dermal skin protectant and carrier and protectant comprises a first dimethicone product having a first viscosity. FIG. 1 details a generic formula for dimethicone, with "n" number of repeating units. The greater the number of repeating "n" units, the greater the viscosity of the material. The dermal skin protectant and carrier and protectant further comprises a second dimethicone product, having a second viscosity, wherein the second dimethicone product's viscosity is at least 2.0 million cP greater than the viscosity of the first dimethicone product. The cP unit (centipoise) is a unit of dynamic viscosity. The combination of the two viscosities provides a material that, when applied to a skin surface, provides for a barrier, and has strong mucoadhesive properties, wherein the material will adhere to a dermal skin surface and is resistant to being removed because of strong adhesion. This material forms a barrier comprised of the dimethicone materials on skin surfaces. However, it also serves as a reservoir for excipients for treatment of one or of many of the afflictions described herein.

Application of the material onto the skin provides for a barrier that provides for a level of protection against elemental exposures. For example, the dermal skin protectant and carrier and protectant may be in the form of a paste, a gel, a foam, a liquid, a solid, a polish, a varnish, a lacquer, crème, ointment, or the like for direct application, or may be added to a bandage, a wound dressing, or added to a suppository, a feminine hygiene product such as a tampon or a pad, or may be in solid powdered form. Each of these forms allows application onto a skin surface, wherein the dermal skin protectant and carrier and protectant forms a protective coating on the skin surface. Thereafter, the materials admixed (or dissolved into) the dimethicone are released into the dermal tissue, where the efficacy of such products allows for treatment of the underlying skin affliction.

As used herein, the term "active agent," "additive," or "excipients" are used together to mean any material added to the topical carrier product of the present embodiments other than the dimethicone components. This term includes additional excipients and therapeutic agents, but also includes flavorants, colorants, preservatives, binders, carriers, viscosity enhancing materials, and the like that may be suitable for dispersion from the material or for formulating a composition suitable for the intended use in one or more various forms.

As used herein, the term "therapeutics" means, a compound or compounds added to the material for delivery to the surface of application or into the skin for enacting some therapeutic response to the skin, nails, or hair.

For example, in certain embodiments, a therapeutic may include, as nonlimiting examples: benzalkonium chloride, cetylpyridinium chloride, nystatin, sulfur compounds, colloidal silver compounds, ferric subsulfate, hemostatic agents including fibrinogen, thrombin, and chitin, mucositis treatments, sulfur compounds, promote healing, bone growth, antimicrobial, topical anesthetics including but not limited to benzocaine or lidocaine, antifungal, $CoQ_{10}$, vitamins such as vitamin D, chlorhexidine, monographed compounds approved by the FDA, chitosan (hemostatic/antimicrobial property), hemostatic materials, anti-inflammatory, topical steroid, antihistamine, THC/CBD, silver nitrate, peppermint, cinnamon, wintergreen, chlorine as used for scent and antifungal or antibacterial oils, antifungal, skin protection; deodorant, anesthetic, steroid, essential oils, odor masking or preventing, skin protectant, antimicrobial and antibacterial, pain relief, zinc oxide, small molecules for therapeutic treatment of mammals, nitroglycerin, testosterone or other steroids, nicotine, hormones, nausea treatment, estrogen replacement, fentanyl patch, transdermal scopaline, hypertensine, MAOI antidepressant, ADHD, vitamin $B_{12}$, 5-THP, retin-A, and combinations thereof.

A key component of the of dermal skin protectant and carrier of the present disclosure is dimethicone, also known as polydimethylsiloxane or PDMS, which is a silicone-based polymer. Dimethicones have wide ranging uses, for example in antiperspirants, skin creams, skin lotions, suntan lotions, bath oils, hair care products, lubricant, and as coatings for oral products. Skin care products have a wide range of uses and dimethicone is relied upon for its properties as a base for a wide range of cosmetic formulations, its hydrophobicity, range of viscosities, lubricating properties, low surface tensions, clear, odorless, inert, and that it is miscible with a wide range of other materials.

Indeed, dimethicones of various viscosity are relied upon in many cosmetic formulations where it is used for filling in uneven texture and fine lines, such as in primers, foundations, or lotions. Furthermore, as a silicone oil, it provides a protective cover on skin such as with suntan lotions or other skin lotions.

Dimethicones are also used in hair care products to provide smoothness, specifically in conditioners or detangling products. Indeed, dimethicone assists with smoothing hair and in reducing or removing knots in hair. Furthermore, in many hair care products, dimethicones are utilized to leave a shine or sheen on hair.

PDMS has the typical formula:

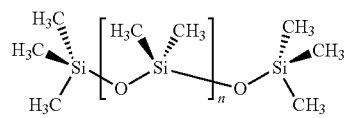

with the number of "n" repeating units impacting the viscosity of the material. Dimethicone products are often sold in various formulations by their viscosity. Here, we combine at least two different viscosity dimethicone, one having a viscosity of between about 1,000 cP and 50,000 cP and a second having a viscosity of between about 2.0 million cP and 3.0 million cP, and preferably about 2.5 million cP. When purchasing these materials, a typical certificate of analysis will provide a viscosity as determined by a rotational test, and each certificate of analysis will provide a specification limit for the material, usually within about 10%, or about 5%, or about 1% of a stated specification. For example, for a 2.5 million cP viscosity, the materials used in the embodiments herein comprised a specification range of 2,312,500 to 2,687,500 cP based upon actual analysis of the solid materials.

The FDA has approved dimethicone for personal care products and generally is considered safe for use. Indeed, the FDA lists at least 16 entries for topical, transdermal, and oral applications. Accordingly, dimethicones have a known and expected safety profile with the FDA.

The difference in viscosity for dimethicone comes simply in the number of repeating polymer units of the molecule. For example, a polymer having a greater number of repeating units will tend to restrict movement and thus will have a greater viscosity than one with a lower number of repeating units. However, when purchasing these dimethicone products commercially, in nearly every example, the materials are sold by their viscosity, with a range or variation of about 1-10% of the stated viscosity. Accordingly, we define them herein by their viscosity as would be understood by those of skill in the art.

In creating a formulation for the present dermal skin protectant and carrier products, several considerations must be evaluated, namely: rate or release of active ingredients, adhesive forces, as well as the aesthetic and tactile response of the material to generate a superior product. As detailed in Formulations 1-9 below and in Table 3, we tested two different basic formulations, one using a 1,000 cP dimethicone component with the 2.5 million cP dimethicone, and a second where the 1,000 cP dimethicone was replaced with a 12,500 dimethicone. We also tested variations using a 25,000, and 50,000 cP mixed with the 2.5 million cP dimethicone. Finally, we tested the 1,000 and 12,500 dimethicones with a lower 1.5 million cP dimethicone.

We tested variations of dimethicone admixed with a second dimethicone, in various ratios to evaluate the combination that provided the greatest and least force of adherence.

Adherence and release profile are both instrumental in generating a skin protectant material having an appropriate adherence to the skin and a proper release rate based on that adherence. For example, where a material is likely to be quickly washed off, Table 3, below, details several different formulations of the present disclosure, each having a different amount of forces (peak adhesive forces) and (total work of adhesion) which provide for a value of each material with respect to its adhesive forces. These values are calculated using benzalkonium chloride as an active ingredient, but our tests confirm that additional excipients or removal of the benzalkonium chloride does not greatly alter these values and thus the values in Table 3 can be utilized to understand the impacts of different amounts of two dimethicone materials when combined. Those with a greater adhesion are going to typically remain on a skin surface for a greater period of time than one with a lower peak adhesive force. Accordingly, formulations using a greater percentage of the 2.5 million cP dimethicone have a much greater peak adhesive force and thus will have greater adherence to the skin surface.

Figure 2:
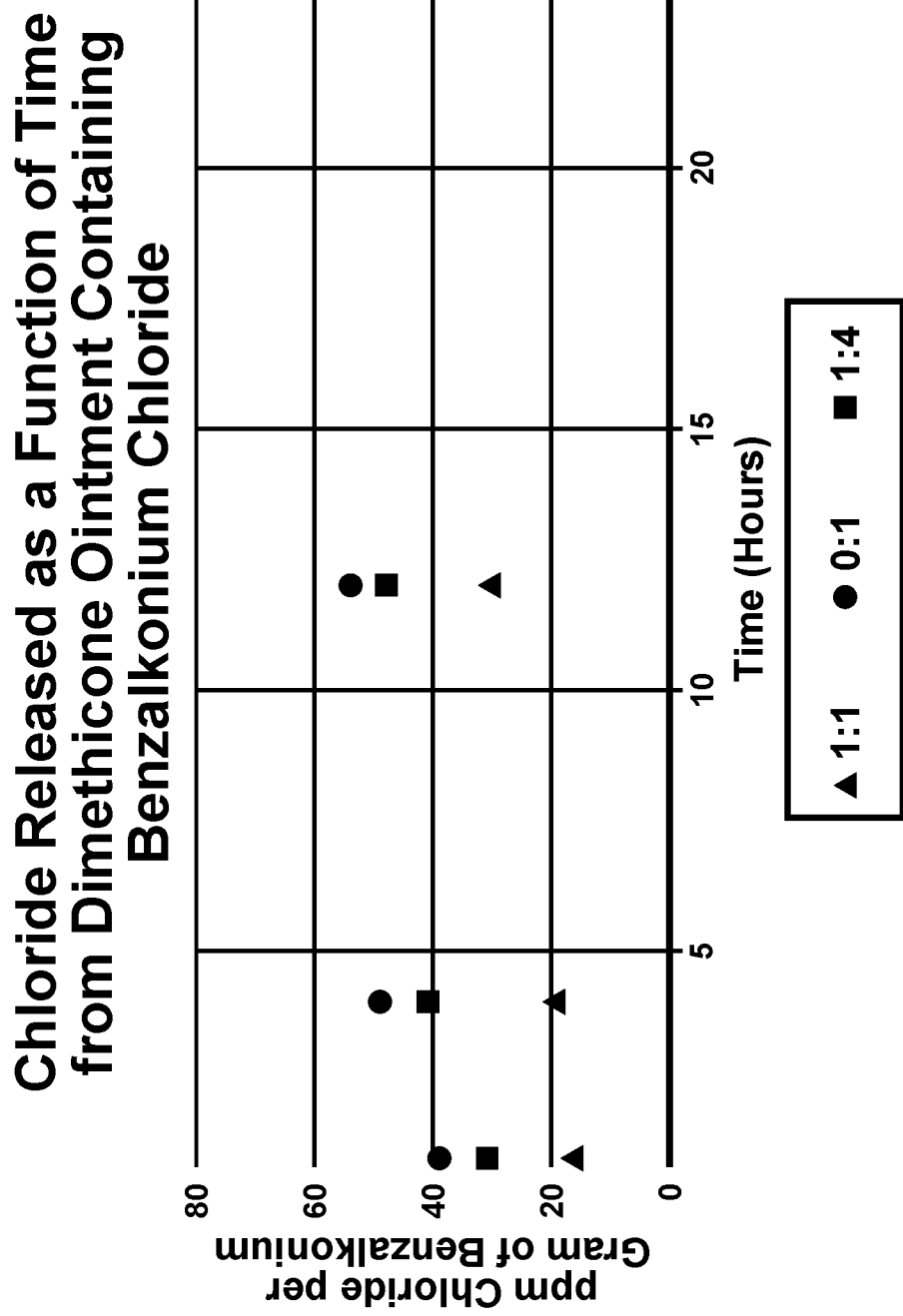
FIG. 2 depicts a release profile of several different blends of the present disclosure, with regard to release of benzalkonium chloride over a 24-hour period.

At the same time, for many applications, there must be a balance between the peak adhesive forces and the rate of dissolution of the benzalkonium chloride (or other active ingredients) from the material. FIG. 2 details a rate of dissolution of an active agent, in this case, benzalkonium chloride, from three different formulations, and provides that those with greater amounts of the 2.5 million cP dimethicone have a slower dissolution rate of the benzalkonium chloride from the carrier. At a 1:1 ratio the chloride release rate is nearly ½ of that with the other two tested release profiles of the present disclosure. Accordingly, while the product with only the 1,000 cP dimethicone had the fastest release profile from 0-5 hours, at 24 hours, its total release was nearly identical to that of the 1:4 ratio product. And, the 1:4 ratio product has a dramatic and significant improvement in adhesion as compared to the 1,000 cP material.

At 24 hours, the release profile of the 1:1 ratio product reached over 40 ppm chloride per gram of the dermal skin protectant. The importance of these release profiles is to evaluate the twofold concern of a release rate that allows for uptake of the released benzalkonium chloride (active agent), while balancing the need for adhesion to maintain the material on a skin surface. For example, if the 1,000 cP material alone washes off of a skin surface too easily, for example within 30 minutes, its fast rate of release is insufficient because it would not have sufficient time to allow for release of the active agents, or to provide the desired skin protectant properties. Thus, a skin protectant that has strong adhesion is desirable as it is necessary to both maintain the material on the skin surface and to allow for timed release of the active ingredients.

Figure 3:
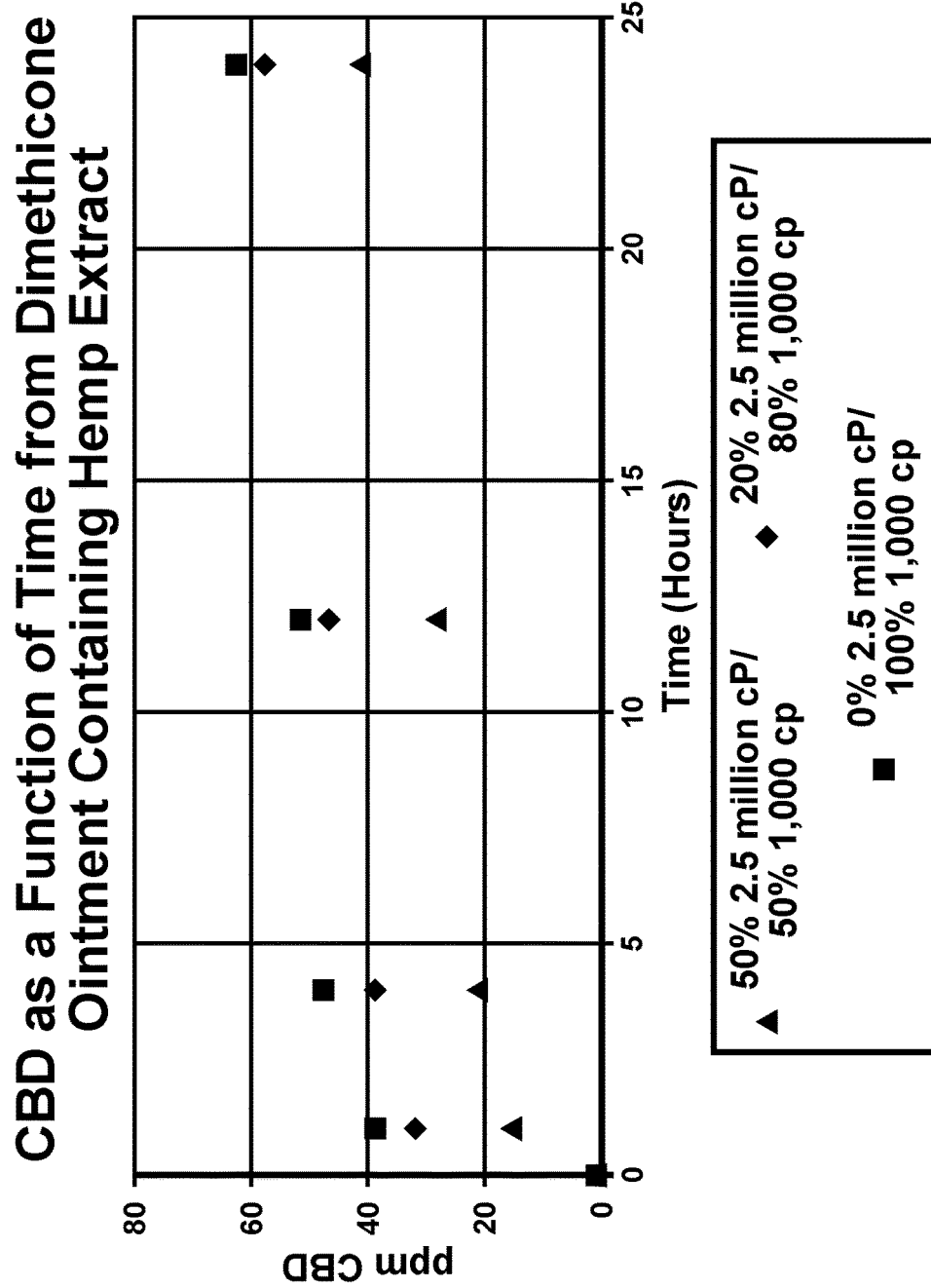
FIG. 3 depicts a release profile of several different blends of the present disclosure, with regard to release of CBD over a 24-hour period.

To confirm the release profile, a second active agent was tested to determine release profile as depicted in FIG. 3, namely the release of CBD from the material. FIG. 3 details a highly similar set of findings as compared to those of FIG. 2, namely that the lowest viscosity materials have a faster release profile, but that the total release profile is near identical to that of products that use a 4:1 ratio of low viscosity to high viscosity dimethicone. Indeed, while not depicted in the figures, fluoride release was also tested in an analogous study, and also confirmed the same general principals with regard to release. Thus, several different materials all show analogous and consistent release profiles from the material.

For purposes of a crème, paste, gel, liquid, solid, or foam for application to a skin surface, the dermal skin protectant and carrier of the present disclosure must also have a profile that allows for application of the material at room temperature. Indeed, ease of application is necessary to ensure that the material is correctly applied, but also to aid in its ultimate use. A material that needs to be heated or chilled or applied with special applicators is likely to face burden from professionals (for materials applied by a medical professional) or face even lower acceptance if over-the-counter products require special handling for application. Indeed, as with many products, simplicity is essential to proper use of the material. Thus, the material is preferably in the form of a gel like or paste like consistency which can be applied directly to a skin surface. For example, an applicator may apply a thin film of material, like those in solid or gel like deodorant products. Alternatively, a material may be in a tube and squeezed out for application, or in ajar, like a topical crème. Finally, the material, once applied to the skin surface the dimethicone adheres to the skin surface. The material will generally remain on the surface until it has been wiped off intentionally or unintentionally through friction and contact with clothes or other surfaces.

The combination of a first and second silicone dimethicone materials provides for a smooth and clean tactile coating on skin surfaces. Indeed, the combination of the dimethicone products generates a barrier skin protectant that also aids in forming a lubricating or smooth texture on the skin surface. Thus, the formation of the protectant barrier layer on the skin surface will allow for a protectant layer to enable healing of the underlying skin. Furthermore, as the protectant layer is on the skin surface, the excipients or specific active therapeutic agents are released from the protectant layer into the skin and aiding in the relief or treatment of the tissues. Excipients (and/or therapeutic agents) will be released from the carrier material unless they are macromolecular additives that entangle with the dimethicone itself.

The primary components of the skin protectant and carrier material are the first and second dimethicone materials. In certain embodiments, a third or more dimethicone(s) may be further added. In preferred embodiments, to this combination of dimethicone materials is added at least one excipient. For example, depending on the desired texture and desired form of application, it may be suitable to add in a bulking agent or texturizing agent, a flowing agent. Certain examples might include a natural or synthetic wax, such as beeswax or a plant-based wax, fats, oils, Gantrez® (synthetic, alternating copolymers of methyl vinyl ether (MVE) and maleic anhydride), or other excipients added for aiding with the texture and physical properties of the material once formed.

Benzalkonium chloride, for example, may be added as a therapeutic material, for its use as an antiseptic and disinfectant, and for its preservative properties. However, when used in sufficient concentrations, its use as an antiseptic on skin tissue and can help to reduce bacterial populations that may be present, for example on a wound.

Accordingly, when using the present material on a skin surface, in addition to the ability to cover, coat, and provide a barrier, the inclusion of certain healing promoting agents can improve the rate of healing and improvement of the skin. Those of skill in the art will recognize the number of agents for promoting healing as identified in the specification, which can be advantageously admixed into the material.

When considering the use of the material on a skin surface with an open wound, or a scabbed wound, care for that damaged tissue is important for healing, both for speed of healing and for reducing infection, and also for reducing the presence of scar tissue. Herein, we can utilize the material as described and admix additional active ingredients to aid in the promotion of healing, reduction in infection and use of certain materials that aid in the reduction of scar tissue. For example, those of skill in the art will recognize that antibacterial materials would reduce topical infection, and other materials may cleanse the wound. Furthermore, certain materials, including certain essential oils, shea butter, and similar materials coat, protect, and allow the wound to heal, but also to promote collagen formation to reduce wrinkles or scar tissue.

In certain instances, the wound may also be painful and, therefore, it makes sense to utilize an anesthetic ingredient within the material to reduce pain. For example, benzocaine and lidocaine, and similar materials can be added for contact or timed release to reduce surface pain. Certainly, these materials may be suitable for release to skin surfaces, even without the presence of a wound to provide immediate relief of pain at the skin surface.

In certain aspects, pain may stem not just from a wound but where the pain is due to long-term muscular-skeletal issues, additional pain medications are indicated to reduce pain. For example, opioids have been used for centuries to reduce pain. This includes the use of opium, which has been cultivated for millennia. First opium poppy cultivation and earliest references to opium use is often traced to the era around 3,400 BC in Mesopotamia. Ancient Sumerians understood that the bright red poppies had significant medical powers and referred to the plant as hul gil or "the joy plant." Opium cultivation spread to the ancient Greeks, Persians, and Egyptians from that time, through the period of ancient kinds in Egypt. Even Homer referred to opium's powers in the Odyssey. Opium spread to China and Easy Asia along the Silk Road, and its use spread to many of the nations that now continue its cultivation. Indeed, in the 1700s wars were fought over land and territory for growth of this plant.

In modern society, opioids were frequently consumed by smoking opium, for example as workers toiled in the American west, the 1849 gold rush, and other similar ventures in the 1700 and 1800s. Ultimately, raw opium was synthesized into materials we know about in more modern medicine, including morphine and heroin. However, while morphine continues use in medical industry, heroin, because of its strong chance for abuse, is infrequently utilized. Other analogs from the opium poppy have been developed and are also in use, including some synthetic derivatives. Each of these agents can be used in certain applications where they are imparted into the material and allowed to release as an active agent. For example, a slow release may allow for a better pain management over a long period of time for certain users. In other applications, faster release profiles may be utilized when immediate pain medication would be needed.

In certain instances, it is necessary to dry a skin surface to allow for adherence with another material. Accordingly, those of skill in the art will recognize the need for and use of drying agents to aid in such pursuits.

As indicated above, the use of the materials indicated herein on skin tissues is applicable when there are open wound issues. Therefore, it is advantageous to apply certain hemostatic materials to the wound to increase the ability to stop bleeding and increase healing of the wound. Accordingly, application of hemostatic active ingredients into the dimethicone materials allows for release of these hemostatic ingredients.

Figure 4A:
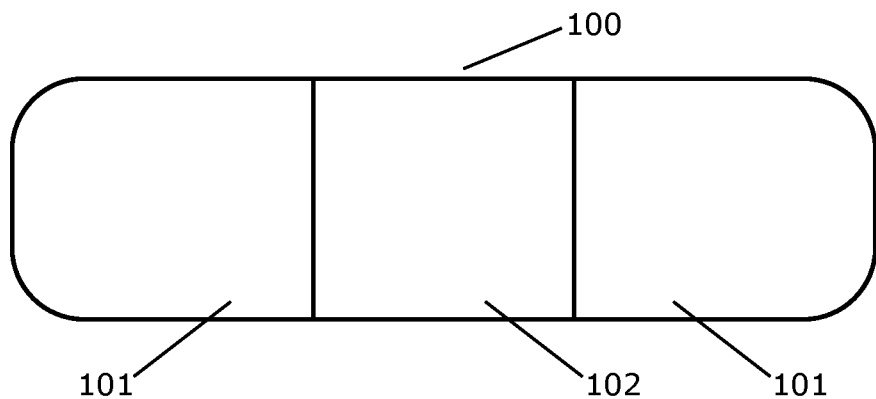
FIGS. 4A-4C, depicts an embodiment comprising a bandage showing certain layers of the material having a skin protectant therein.
Figure 4B:
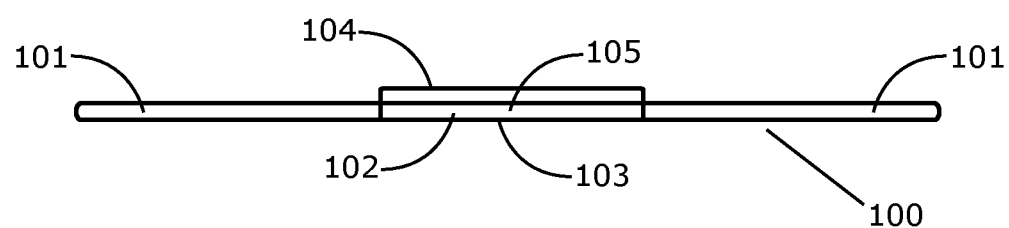
Figure 4C:
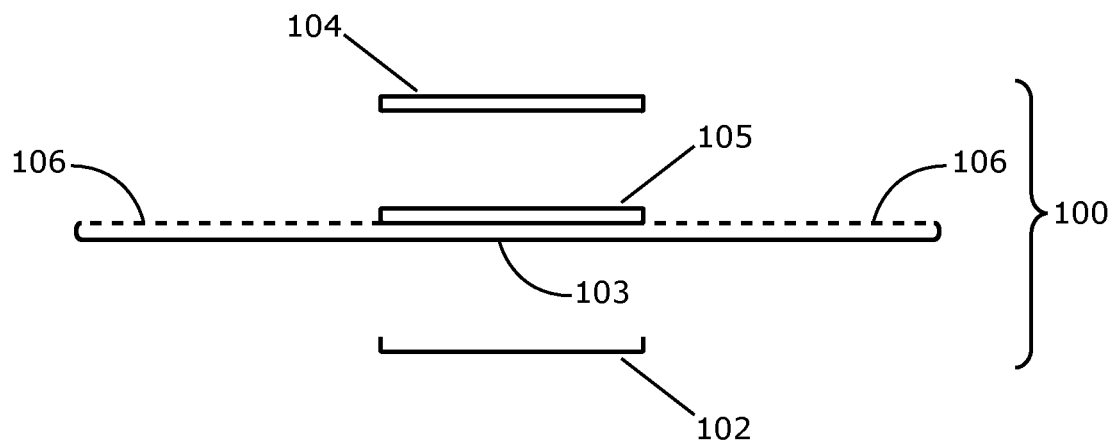

For example, as depicted in FIGS. 4A-4C, in FIG. 4A, depicts a bandage (100) comprising two adhesive elements (101) that sandwich a wound covering element (102). FIG. 4B provides a side profile of the layers of the bandage (100), comprising a backing layer (103), an adhesive (101) or a nonadhesive attachment method (106) as in FIG. 4C, a covering element (102) comprising a top coating (104) and a middle coating (105). FIG. 4C then depicts these layers of covering element (102) as separated to show greater clarity.

For example, the top coating (104) may be an absorbent material, such as cotton or other suitable natural or synthetic polymer. This adhesive material may further comprise, be embedded with, or be coated with a material of the present disclosure comprising the dimethicone components. Alternatively, no dimethicone material is added in this layer.

The middle coating (105), like the top coating (104), may comprise an absorbent material or may comprise the dimethicone material of the present disclosure. In such embodiments, the dimethicone material may comprise any number of the active ingredients and excipients as disclosed herein, in order to aid in covering the wound, allowing for healing of the wound, and for absorbing fluid flow from the wound.

In certain embodiments, inflammation within the body is extremely painful or makes it difficult or impossible to move. We can utilize the dimethicone materials as a carrier for anti-inflammatory active ingredients to allow for release of anti-inflammatory ingredients at the site of the injury. Because of the long-lasting effects and ability of the materials herein to stay adhered to the skin, the anti-inflammatory ingredients will release into the skin. Modifying the excipients, the amounts of each dimethicone, and the relative viscosity of each dimethicone can control the rate of release and this will allow for long duration release of the anti-inflammatory to reduce swelling, irritation, and inflammation at the site of the injury.

However, in certain cases, anti-inflammatory ingredients are not strong enough to address the underlying issue. One medication that is frequently used as the next strongest material is a topical steroidal application. There are numerous approved steroidal compounds, corticosteroids that can be admixed into the dimethicone material for release. For example, hydrocortisone, desonide, fluocinolone acetonide, alclometasone dipropionate, hydrocortisone valerate, prednicarbate, fluticasone propionate, flurandrenolide, desoximetasone, mometasone furoate, betamethasone valerate, fluocinonide, halicinonide, diflorasone diacetate, betamethasone dipropionate, halobetasol propionate, clobetasol propionate, flurandrenolide, and other similar corticosteroids, salts, or their derivatives.

In addition to reducing inflammation, corticosteroid compounds might be used for other applications, including to combatting rashes, dermatitis, itching, eczema, psoriasis, and other similar injuries. Other steroids, such as testosterone, progesterone, estrogen, and similar steroids have other therapeutic uses and, these too, can be used for topical purposes.

Certainly, these steroids or corticosteroids can be applied as a solid, liquid, gel, crème, aerosol, or other form as indicated herein. These allow for application to skin surfaces and then release of the material through the skin, or onto the skin. For example, nasal applications would allow for a coating of the nasal passages, providing a lubricant to the nasal passages, but also allow for targeted delivery of medication to this location. For example, gels, balms, aerosols, liquids, and the like could be formulated for nasal application. A solid could be applied to the tip of the nose or openings of the nasal passages to impart these properties, and also include other excipients, for example certain essential oils, UV protectant materials, or simply additional skin protectant materials to prevent dry, red, and cracking nasal tissues.

Fungal infections are prone in several areas of the body, including those commonly referred to as jock itch, athlete's foot, or other similar names. Furthermore, additional fungal, bacterial, and/or viral infections are prevalent on or under the nails, or in around the feet, toes, and joints of the body. Application of the present dimethicone-based material and including an antifungal composition can reduce the impacts of the skin irritation and provide an antifungal to eliminate the underlying fungus. Furthermore, additional excipients to reduce moisture, to sooth the skin irritation, and to heal the skin can be appropriately tailored for the intended use of the therapeutic.

The nails of the hands and feet themselves are prone to infection from fungal, bacterial, or viral attacks, as well as the skin adjacent to or under the nail. The nail matrix is where nail cells multiply and keratinize before being incorporated into the fingernail or toenail. The cuticle is a fold of skin where the finger or toe meets the nail, and protects the matrix, the area under the skin below the nail fold and covers the lunaula. The nail plate is the nail itself, and below that is the nail bed, or the soft tissue under the nail. Nail infections, specifically those of the nail include a variety of fungal infections such as onychomycosis, including distal lateral subungual onychomycosis (DLSO) where the fungus spreads from the skin and invades the underside of the nail. White superficial onychomycosis (WSO) is another infection caused by the fungi directly invading the surface of the nail plate and secondarily infecting the nail bed. Proximal subungual onychomycosis (PSO) is where fungi invade the cuticle and the nail fold. Endonyx onychomycosis (EO) is where the fungi reach the nail via the skin and invade the nail plate. Additional fungal infections may come from yeast (*Candida*), which also affect both the nail itself, as well as the dermal tissues surrounding and supporting the nail.

Bacterial infections of the nail, including but not limited to paronychia can impact both the nail plate and the surrounding tissues, through bacterial attack. Bacteria including *Pseudomonas aeruginosa* may be the cause for certain infections including green nail syndrome. Other bacterial infections may include staph infections.

Nail tissues may also be inundated with yeast and mold spores. In certain applications it is necessary to provide therapeutic materials that can eliminate mold or yeast spores or prevent them from colonizing certain nail tissues.

For many nail treatments, the goal is to treat not just the visual infection, but to eradicate the microbial collection that forms in the dermal tissues under or adjacent to the nail. Materials applied to the nail and adjacent dermal skin allow for the therapeutics to reach the damaged or infected tissue and to treat the issue. Certain materials can be applied as a nail polish, which incorporate a broad spectrum antimicrobial agent or agents to treat the fungal, bacterial, mold, yeast, or viral infection. For example, Ciclopirox has been previously utilized in nail polishes for topical application, which allows penetration through the nail plate and into the nail bed, to treat the underlying fungus. The embodiments herein can be utilized in a lacquer or nail polish application, the creates additional adhesion to the nail and dermal tissues surrounding or under the nail to release therapeutics to treat the underlying issues.

Additional fungal infections are also prevalent in and around the lips and mouth, for example thrush. The embodiments of the present disclosure can be applied to these skin surfaces and release a therapeutic to the lips and outer surfaces of the mouth to treat this and other fungal infections. Similarly, bacterial and viral infections, including herpes can be treated with antibacterial or antiviral therapeutics, or the symptoms alleviated with certain materials that can be applied through the dermal material described herein. Furthermore, lip-based care may include moisturizing agents and sunscreen agents that, because of the propensity for being easily removed by the tongue and lip movements, would benefit the adhesive nature of the embodiments of the present disclosure, as well as the skin protectant and excipient release from these materials.

Vaginal fungus is also prevalent and a major source of irritation throughout the world. Many current therapeutics require the use of suppositories and, in some cases additional topical applications to reduce and eliminate fungal infections. The material disclosed herein may be utilized both externally and internally for reduction of the fungal infection and treatment of the irritation that is accompanied. For example, the material may aid in lubricant properties, reduction in itching, odor relief, and protection of the skin from raw or irritation effects, while also delivering an antifungal material to treat the source of the irritation.

In certain embodiments, the infections are not fungal but are bacterial in nature. Different therapeutic materials are necessary to treat bacterial agents instead of fungal agents, though there are some agents that are broad spectrum antimicrobial agents that may be effective towards both fungal and bacterial infections. While those bacterial infections of the nail are addressed above, numerous antibiotics are known for treating additional dermal and mucosal skin surfaces. These antibacterial agents are in soaps, cremes, lotions and the like, which are often easily applied. However, in many cases, they are also easily removed from the surface to be treated and thus efficacy is sometimes limited. Thus, the addition of antibacterial agents into the dermal skin protectant material of the present disclosure can aid in the dwelling time of the material on a skin surface and otherwise be utilized to treat or prevent bacterial formation on skin surfaces.

Accordingly, as identified in the embodiments, the material herein provides skin protectant properties through the formation of a barrier on the skin surface and then imparts further properties through release of additional excipients and/or active ingredients. For typical skin issues, including skin irritation, dry skin, rashes, insect bites, bacterial, viral, and fungal infections, etc., this material provides a physical barrier to protect and prevent further damage to the skin, while also imparting therapeutic release to the individual, and to the skin both at the area and through the uptake of the active ingredients through the dermal layer, as opposed to a systemic (oral) approach towards treatment.

In certain embodiments, the material is advantageously utilized as a skin barrier that comprises a UV protection material. Those of skill in the art will recognize the UV material frequently utilized in commercially available sunscreens, wherein the dimethicone material provides barrier protection and coating to the skin, plus a material added as an excipient to prevent further UV damage to the skin surface. Zinc oxide, PABA, ecamsule, cinnamates, benzophenones, avabenzone, and other materials can be utilized in such embodiments.

In certain embodiments, it may be further advantageous to also impart insect repellant excipients into the dimethicone material. For example, the material can be applied as a spray, solid, liquid, gel, provides a barrier to the skin and can include one or more components for insect repellant, including DEET, cyfluthrin, permethrin, pyrethroids, methyl anthranilate, benzaldehyde, dimethyl carbate, dimethyl phthalate, ethylhexanediaol, icardin, indalone, IR3535, methofluthrin, SS220, tricyclodecentyl allyl ether, 2-undecanone, birch, beautyberry (callicarpa), myrica Gale, catnip oil, nepetalactone, citronella, lemon eucalyptus, neem oil, lemongrass, tea tree oil, tobacco, and other known natural oils for repelling pests and insects.

In certain embodiments comprise a portion of a hemp extract. Hemp extract shall mean a material comprising a portion of extracted material from the hemp plant, containing at least one or more of certain cannabinoid or terpene molecules. Specifically, hemp extract is conceived to comprise one of either cannabidiol (CBD) or delta-9-tetrahydrocannabinol (THC). In certain embodiments, a log THC Hemp extract means one having less than 0.30% THC. A high THE Hemp extract means one comprising THC of more than 0.30% THC. Typically, extracts are ethanol or $CO_2$ extracted from can *Cannabis* plants and comprise a plurality of cannabinoid and terpene molecules. These can be diluted with another carrier oil or solvent, as necessary.

Cannabinoids, including CBD and THC-infused topicals readily enter the skin layers. Accordingly, the carrier materials defined herein are effective at delivering the cannabinoid compounds and other compounds to the skin effective at relieving pain and inflammation in the area in which they're applied. Since cannabinoids don't enter the bloodstream with this intake method, topically applied THC has a very limited ability to cross the blood-brain barrier (unless applied internally), and thus has little to no psychoactive properties. Accordingly, these topically applied materials are effective in treating the dermal layers and for delivery of therapeutics and other materials topically and to these skin layers, for example, for treating those afflictions that are topical and dermal in nature, and for relieving ailments such as those on or in the skin.

Thus, embodiments herein can utilize the materials for topical applications to slowly release the active cannabinoid or terpene from the dimethicone carrier for treatment of the body. For example, application of a topical dermal material to the skin surface allows release of CBD molecules to the skin surface for therapeutic effects. Additionally, the CBD can be applied to the nasal passages for intake through the nasal mucosa. However, the dermal materials can be applied to the body wherein the use of the hemp extract, and the varying concentrations of various cannabinoid materials therein, allows for the hemp extract components to be delivered to the body. For example, for its use in reduction of seizures, application to the body may allow for appropriate slow dosing. For reduction in nausea, headache, or ache and pain, the topical application can target the areas for treatment in the material as described herein.

Nicotine patches, gums and other dosing forms are widely utilized as smoking cessation products. The materials of the embodiments herein can be utilized as a carrier for nicotine and applied topically to provide nicotine replacement. Certain formulations can provide slow release, while others can give a fast release. In certain embodiments, the nicotine can be a food material, such as gum or a lozenge, or applied topically to the body.

Hormone replacement therapies assist both men and women who have a need for replacement of sex hormones that are missing or need to be augmented for any reason. While many hormones are provided for birth control, and others for low testosterone or low or improper estrogen reasons, hormones are also utilized in gender applications for those who transition. Again, the therapy can be provided as in the dosing forms as described herein.

Nausea continues to be a major issue for people, both due to medications and to environmental concerns. Certain medications or treatments include nausea as a frequent side effect. At the same time, environmental concerns, including seasickness, motion sickness, altitude sickness, etc., are faced by persons without other medical treatments. Each issue may be resolved by various active ingredients to reduce the occurrence of the nausea symptoms or to better manage the symptoms that do occur, for example with transdermal scopaline.

Hypertension remains a prevalent issue with the ever-increasing pace of life in modern society. Suitable therapeutic materials or use of traditional herbal and essential oils can lead to reductions in stress that can reduce or alleviate hypertension. In other cases, more targeted medications are necessary to control blood pressure.

Increase in blood pressure, and other health factors can also lead to angina, which may need medication to be controlled. For example, we can utilize the dimethicone delivery vehicle for application of certain Nitroglycerin molecules.

Those of skill in the art will therefore recognize from the sizeable list of examples defined herein, as well as the examples defined in the nonlimiting tested embodiments below, that many small molecules are suitable for therapeutic delivery from the dimethicone delivery vehicle of the present disclosure. Indeed, as envisioned, the material herein can serve as a carrier and a reservoir and is applied topically to a skin or mucosal surface and the therapeutic is transferred transdermally to the skin for uptake by the body.

However, the embodiments also identify nontherapeutic purposes, wherein the material is a carrier for flavors, colors, glosses, UV protection, insect repellant, etc. For example, lip care might include a gloss, a flavor, a pigment, or another soothing or coating material. Thus, it can be both a simple barrier, or added with an active ingredient, just like common over-the-counter materials in the current lip care line of products.

Formulation of the Dimethicone Material

The dermal skin protectant and carrier and protectant material can be formulated under conditions that will prevent the growth of bacteria or prevent spoiling. Certainly, through particular processing or post processing steps or through the inclusion of certain antibacterial agents, increased safety and an increased shelf life may be provided. The material can be formulated and then sterilized under ordinary procedures know to those of skill in the art in the field of dermal care products, including heat, ozone, ethylene oxide, radiation, etc. Alternatively, no sterilization process is necessary.

In preferred embodiments, the material is formulated as a liquid, a paste, or a gel, in each case, having a consistency sufficient to be applied to a skin surface. Other formulations may have a more solid like consistency, wherein an applicator may allow for application of a thin layer, similar to application of deodorant or lip protectants. Other applications may include an aerosol, wherein small particles are placed under pressure and can be sprayed onto a skin surface. Other forms, known to those of ordinary skill in the art can be utilized to generate a protective layer of the material onto a skin surface.

Methods of Manufacture of the Dimethicone Dermal Skin Protectant and Carrier Product The mixture of two different viscosity dimethicone products, specifically of those having such a dramatic difference in viscosity provides significant hurdles in manufacturing and mixing of components. Indeed, one cannot simply add all the components to a mixing bowl and mix/stir the components to create the instant formulations. Several different protocols were tested to allow for thorough mixture of the components until an appropriate process was generated.

As an example, the components of Example 1 below, were tested in several different mixing applications. Initially, all components were placed together in a single mixing vessel and mixed with a magnetic stirring rod. Mixture was impossible due to the viscosity of the material. A further test attempted to use a spinning/rotating mixing blade. However, the viscosity of the material made this difficult, except for the smallest amounts of the 2.5 million cP material, and the blades introduced significant amounts of air into the product. We settled on a bladeless mixing system that utilizes centripetal forces to aid in mixing, and these strategies proved effective for mixing of the two different viscosity silicone materials and the additional excipients in the examples below.

EXAMPLES

Example 1

A Flacktek mixer was used to mix the following compounds: dimethicone (2.5 million cP); dimethicone (1,000 cP); benzalkonium chloride. Initially, 17.1 grams of 1,000 cP dimethicone was added to the mixing cup. Next 1 gram of benzalkonium chloride was added to the mixing cup. The two compounds were mixed at 3,000 RPM for 10 minutes. Next 1.9 grams of the 2.5 million cP dimethicone was added in 5 increments of 0.38 grams. After each increment was added, the formulation was mixed for five-minute increments.

Subsequent formulation examples were prepared following the same procedure as Example 1. The following table lists the ratio of components used in the specific formulation example.

TABLE 1

| Formulation Example | Mass (g) of 1,000 cP Dimethicone | Mass (g) of 2.5 million cP Dimethicone | Mass (g) of Benzalkonium Chloride |
|---|---|---|---|
| 2 | 15.2 | 3.8 | 1 |
| 3 | 13.3 | 5.7 | 1 |
| 4 | 11.4 | 7.6 | 1 |
| 5 | 9.5 | 9.5 | 1 |

Example 6

A Flacktek mixer was used to mix the following compounds: dimethicone (2.5 million cP); dimethicone (12,500 cP); benzalkonium chloride. Initially, 17.1 grams of 12,500 cP dimethicone was added to the mixing cup. Next 1 gram of benzalkonium chloride was added to the mixing cup. The two compounds were mixed at 3,000 RPM for 10 minutes. Next 1.9 grams of the 2.5 million cP dimethicone was added in five increments of 0.38 grams. After each increment was added, the formulation was mixed for five-minute increments.

TABLE 2

| Formulation | Mass (g) of 12,500 cP Dimethicone | Mass (g) of 2.5 million cP Dimethicone | Mass (g) of Benzalkonium Chloride |
|---|---|---|---|
| 7 | 15.2 | 3.8 | 1 |
| 8 | 13.3 | 5.7 | 1 |

TABLE 2-continued

| Formulation | Mass (g) of 12,500 cP Dimethicone | Mass (g) of 2.5 million cP Dimethicone | Mass (g) of Benzalkonium Chloride |
|---|---|---|---|
| 9 | 11.4 | 7.6 | 1 |
| 10 | 18 | 1 | 1 |
| 11 | 18.5 | .5 | 1 |

The mucoadhesion of the nine dimethicone formulations above were measured using the Tensile Test method as described in the literature. A Brookfield Conn.3 Texture Analyzer instrument was used at room temperature (23±1° C.). 20 grams of sample was used in a container and measurements were made within 2 minutes of filling the container. The Peak Adhesive Force was measured (n=6) for each formulation. These values are reported in Table 3 below. The Total Work of Adhesion was measured (n=6) for each formulation. These values are reported in Table 3 below. A larger negative number indicates a greater peak adhesive force or a greater total work of Adhesion under these tests.

TABLE 3

| Formulation | Peak Adhesive Force (N) | Total Work of Adhesion (N · sec) |
|---|---|---|
| 1 | −1.5 ± 0.03 | −0.68 ± 0.02 |
| 2 | −5.4 ± 0.15 | −2.0 ± 0.03 |
| 3 | −12.9 ± 1.2 | −5.3 ± 0.09 |
| 4 | −28.5 ± 2.7 | −10.8 ± 0.32 |
| 5 | −41.2 ± 1.7 | −16.5 ± 0.60 |
| 6 | −9.9 ± 0.33 | −3.7 ± 0.06 |
| 7 | −13.8 ± 0.28 | −6.6 ± 0.14 |
| 8 | −18.6 ± 1.7 | −10.9 ± 0.30 |
| 9 | −35.3 ± 4.0 | −16.0 ± 0.65 |

Dimethicone Antifungal Delivery Examples

A Flacktek mixer was used to mix the following compounds: dimethicone (2.5 million cP); dimethicone (1,000 cP); Nystatin. Initially, 10.1 grams of 1,000 cP dimethicone was added to the mixing cup. Next 0.4 grams of Nystatin was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); Nystatin; *Aloe vera*. Initially, 10.1 grams of 1,000 cP dimethicone was added to the mixing cup. Next 0.1 grams of Nystatin was added to the mixing cup. Next 0.2 grams of *Aloe vera* was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); clotrimazole. Initially, 10.1 grams of 1,000 cP dimethicone was added to the mixing cup. Next 0.1 grams of clotrimazole was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Burn Treatment Delivery Examples

A Flacktek mixer was used to mix the following compounds: dimethicone (2.5 million cP); dimethicone (1,000 cP); chitosan; sulfadiazine; silver nitrate; silver nanoparticles; benzocaine. Initially, 10.1 grams of 1,000 cP dimethicone was added to the mixing cup. Next 0.1 grams of chitosan was added to the mixing cup. Next 40 milligrams of sulfadiazine were added to the mixing cup. Next, 40 milligrams of silver nitrate were added to the mixing cup. Next, 40 milligrams of silver nanoparticles were added to the mixing cup. Next, 1 gram of benzocaine was added to the mixing cup. The six compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); silver sulfadiazine. Initially, 10.1 grams of 1,000 cP dimethicone was added to the mixing cup. Next 40 milligrams of silver sulfadiazine were added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); silver nitrate. Initially, 18.1 grams of 1,000 cP dimethicone was added to the mixing cup. Next 40 milligrams of silver nitrate were added to the mixing cup. The two compounds were mixed at 3,000 RPM for 10 minutes. Next 1.5 grams of the 2.5 million cP dimethicone was added in five increments of 0.3 grams. After each increment was added, the formulation was mixed for five-minute increments.

Dimethicone Wound Healing Treatment Delivery Examples

A Flacktek mixer was used to mix the following compounds: dimethicone (2.5 million cP); dimethicone (1,000 cP); bacitracin; neomycin; polymyxin B. Initially, 9.5 grams of 1,000 cP dimethicone was added to the mixing cup. Next 1.45 grams of bacitracin was added to the mixing cup. Next 70 mg of neomycin was added to the mixing cup. Next, 14 mg of polymyxin B was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); bacitracin; polymyxin B. Initially, 17.5 grams of 1,000 cP dimethicone was added to the mixing cup. Next 1.45 grams of bacitracin was added to the mixing cup. Next, 14 mg of polymyxin B was added to the mixing cup. The three compounds were mixed at 3,000 RPM for 10 minutes. Next 1.5 grams of the 2.5 million cP dimethicone was added in two increments of 0.75 grams. After each increment was added, the formulation was mixed for five-minute increments.

A Flacktek mixer was used to mix the following compounds: dimethicone (2.5 million cP); dimethicone (1,000 cP); bacitracin; Epidermal Growth Factor; polymyxin B. Initially, 9.5 grams of 1,000 cP dimethicone was added to the mixing cup. Next 1.45 grams of bacitracin was added to the mixing cup. Next 1 mg of epidermal growth factor was added to the mixing cup. Next, 14 mg of polymyxin B was added to the mixing cup. The four compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); triamcinolone. Initially, 9.5 grams of 1,000 cP dimethicone was added to the mixing cup. Next 100 milligrams of triamcinolone were added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Hemostatic Treatment Delivery Examples

A Flacktek mixer was used to mix the following compounds: dimethicone (2.5 million cP); dimethicone (1,000 cP); tranexamic acid. Initially, 9.5 grams of 1,000 cP dimethicone was added to the mixing cup. Next 1 gram of tranexamic acid was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); chitosan. Initially, 9.5 grams of 1,000 cP dimethicone was added to the mixing cup. Next 1 gram of chitosan was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); human fibrinogen; human thrombin. Initially, 9.5 grams of 1,000 cP dimethicone was added to the mixing cup. Next 0.5 grams of human fibrinogen was added to the mixing cup. Next 1.5 grams of human thrombin was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); kaolin. Initially, 9.5 grams of 1,000 cP dimethicone was added to the mixing cup. Next 1 gram of kaolin was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Monsel's Ferric Subsulfate Delivery Examples

A Flacktek mixer was used to mix the following compounds: dimethicone (2.5 million cP); dimethicone (1,000 cP); ferric subsulfate powder. Initially, 9.5 grams of 1,000 cP dimethicone was added to the mixing cup. Next 4 grams of ferric subsulfate powder was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments before adding in the subsequent incremental amount of the 2.5 million cP dimethicone.

Dimethicone Acne Treatment

A Flacktek mixer was used to mix the following compounds: dimethicone (2.5 million cP); dimethicone (1,000 cP); salicylic acid. Initially, 15.5 grams of 1,000 cP dimethicone was added to the mixing cup. Next 0.4 grams of salicylic acid was added to the mixing cup. The two compounds were mixed at 3,000 RPM for 10 minutes. Next 3.5 grams of the 2.5 million cP dimethicone was added in 3 increments of 1.67 grams. After each increment was added, the formulation was mixed for five-minute increments.

A Flacktek mixer was used to mix the following compounds: dimethicone (2.5 million cP); dimethicone (1,000 cP); benzoyl peroxide. Initially, 9.5 grams of 1,000 cP dimethicone was added to the mixing cup. Next 0.4 grams of benzoyl peroxide was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Hemorrhoid Treatment

A Flacktek mixer was used to mix the following compounds: dimethicone (2.5 million cP); dimethicone (1,000 cP); phenylephrine HCl, pramoxine HCl. Initially, 9.5 grams of 1,000 cP dimethicone was added to the mixing cup. Next 0.1 grams of phenylephrine HCl was added to the mixing cup. The two compounds were mixed at 3,000 RPM for 10 minutes. Next 0.1 grams of pramoxine HCl was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Hemp-Based Extract Delivery System

A Flacktek mixer was used to mix the following compounds: dimethicone (2.5 million cP); dimethicone (1,000 cP); THC. Initially, 18.5 grams of 1,000 cP dimethicone was added to the mixing cup. Next 0.4 grams of THC was added to the mixing cup. The two compounds were mixed at 3,000 RPM for 10 minutes. Next 0.5 grams of the 2.5 million cP dimethicone was added in a single increment and the formulation was mixed for five-minutes.

A Flacktek mixer was used to mix the following compounds: dimethicone (2.5 million cP); dimethicone (1,000 cP); THC, CBD. Initially, 9.5 grams of 1,000 cP dimethicone was added to the mixing cup. Next 0.4 grams of THC was added to the mixing cup. The two compounds were mixed at 3,000 RPM for 10 minutes. Next 0.4 grams of CBD was added to the mixing cup. The three compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); CBD. Initially, 9.5 grams of 1,000 cP dimethicone was added to the mixing cup. Next 0.4 grams of CBD was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone Anti-Inflammatory Delivery System

A Flacktek mixer was used to mix the following compounds: dimethicone (2.5 million cP); dimethicone (1,000 cP); diphenhydramine. Initially, 9.5 grams of 1,000 cP dimethicone was added to the mixing cup. Next 0.2 grams of diphenhydramine was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

A Flacktek mixer was used to mix the following compounds: dimethicone (2.5 million cP); dimethicone (1,000 cP); hydrocortisone. Initially, 9.5 grams of 1,000 cP dimethicone was added to the mixing cup. Next 0.2 grams of hydrocortisone was added to the mixing cup. The two compounds were mixed at 3,000 RPM for 10 minutes. Next 9.5 grams of the 2.5 million cP dimethicone was added in five increments of 1.9 grams. After each increment was added, the formulation was mixed for five-minute increments.

Dimethicone-Based Lip Treatment

A Flacktek mixer was used to mix the following compounds: dimethicone (2.5 million cP); dimethicone (1,000 cP); diphenhydramine. Initially, 18.5 grams of 1,000 cP dimethicone was added to the mixing cup. Next 0.2 grams of Vitamin E was added to the mixing cup, followed by 1 gram of sunflower oil, and 0.1 grams of peppermint oil. The compounds were mixed at 3,000 RPM for 10 minutes. Next 0.5 grams of the 2.5 million cP dimethicone was added in one increment and the formulation was mixed for five-minutes.

In further embodiments, a coconut oil replaced the sunflower oil, and citrus oil was used in place of peppermint oil.

In a further example, 0.2 grams of zinc oxide was further admixed with the peppermint oil. In a further example, tea tree oil replaced the peppermint oil.

A Nail Treatment

A Flacktek mixer was used to mix the following compounds: dimethicone (2.5 million cP); dimethicone (1,000 cP); diphenhydramine. Initially, 17.5 grams of 1,000 cP dimethicone was added to the mixing cup. Next 0.2 grams of Vitamin E was added to the mixing cup, followed by 1 gram of sunflower oil, and 0.1 grams of peppermint oil. The compounds were mixed at 3,000 RPM for 10 minutes. Next 1.5 grams of the 2.5 million cP dimethicone was added in three increments of 0.5 grams. After each increment was added, the formulation was mixed for five-minute increments.

DISCUSSION

As we evaluated each of the formulations, a pattern arose that upon mixing of more of the high viscosity 2.5 million cP dimethicone into the formulations, the ability to work with the material eroded with regard to formulation of liquid, gel, and foam materials. However, as viscosity increased, with the increased amounts of the 2.5 million cP dimethicone, the formulation of solid-based products increased, for example materials that incorporate a gelatin or formation of a solid or near solid material for formulating materials that are suitably applied in a stick applicator form, like many deodorant products. For flowing materials, at a mixture of 100:1 to 4:1 (low viscosity:high viscosity dimethicone), the mixture was easily applied to skin surfaces, for example as a crème, paste, or gel. The consistency allows for application from a tube or a tub of material, or to be ejected from a pump bottle. The material can then be applied to the skin surface, just as a petroleum-based product or lotion would be applied.

However, at a sample of 1:1 ratio of the 1,000 cP and 2.5 million cP dimethicone, the consistency and usability of the material was greatly reduced for liquid, gel, paste, or foam like applications. While at 1:1 ratio, the material would be preferably applied to a skin surface, as a solid like material. However, inclusion of other excipients and even greater amounts of the 2.5 million cP dimethicone generated new materials, that provide for solid applicators, or provide for improved materials for inclusion into a bandage or packing material.

Accordingly, variations in the amount of each of the first and second dimethicone products depended on the ultimate formulation, whether in a liquid, gel, paste, foam, a gummy like, or solid consistency.

Accordingly, based on the data, an optimal formulation comprises a first dimethicone having a viscosity of between 1 and 25,000 cP and a second dimethicone having a viscosity between 2.0 and 3.0 million cP, wherein the materials are admixed with the lower viscosity material comprising between about 10-99% of the mass of the formulation and the higher viscosity material comprising between about 90 and 1% of the mass of the formulation.

An attempt to increase the formulation to greater than 90% of the higher viscosity dimethicone resulted in a material that was simply unworkable. Accordingly, this resulted in a material that could not be easily manipulated, and this reduced the ability to add in active ingredients or to provide any barrier value as a skin protectant. Therefore, the embodiments herein preferably use a range of between 1 and 90% of the higher viscosity dimethicone, with a preferred range of between 1 and 75%, or between 5 and 70%, or between 10 and 65%, or between 10 and 60%, or between 35 and 55%, or between 40 and 50% of the total mass of the formulation.

In certain embodiments a dimethicone-based dermal skin protectant and carrier consisting essentially of a first dimethicone material having a viscosity of between about 1,000 cP and 25,000 cP, and a second dimethicone material having a viscosity of between about 2.0 million and 3.0 million cP; and at least one active agent. In certain embodiments, there is also at least one excipient.

In certain embodiments a dimethicone-based dermal skin protectant and carrier consisting of a first dimethicone material having a viscosity of between about 1,000 cP and 25,000 cP, and a second dimethicone material having a viscosity of between about 2.0 million and 3.0 million cP; one, two or three active agents. In certain embodiments, the carrier comprises one, two, or three additional excipients.

What is claimed is:

1. A dimethicone-based delivery composition comprising: a first dimethicone material having a viscosity of between about 1,000 cP and 25,000 cP and a second dimethicone material having a viscosity of between about 2.0 million cP and 3.0 million cP; and at least one active agent; wherein the concentration of the first dimethicone material is between 47.5% and 92.5% of the weight of the dimethicone-based delivery composition.

2. The dimethicone-based delivery composition of claim 1, wherein the at least one active agent is selected from the group consisting of: an antimicrobial agent, an anesthetic agent, a hemostatic agent, an anti-inflammatory agent, a hemp-based extract, a deodorant, a pain relief agent, a UV protection agent, and combinations thereof.

3. The dimethicone-based delivery composition of claim 2, wherein two or more active agents are combined together in the dimethicone-based delivery composition.

4. The dimethicone-based delivery composition of claim 1, wherein the concentration of the at least one active agent is between 0.1% and 10%.

5. The dimethicone-based delivery composition of claim 2, wherein said antimicrobial agent is an antifungal, antiviral, or antibacterial agent.

6. The dimethicone-based delivery composition of claim 1, further comprising at least one essential oil.

7. The dimethicone-based delivery composition of claim 2, wherein the antimicrobial agent is selected from the group consisting of: benzalkonium chloride, cetylpyridinium chloride, and combinations thereof.

8. The dimethicone-based delivery composition of claim 1, wherein the active agent is an antifungal agent.

9. The dimethicone-based delivery composition of claim 8, wherein the antifungal agent is selected from the group consisting of: clotrimazole, econazole, miconazole, terbinafine, fluconazole, ketoconazole, mophotericin, nystatin, sporanox, difulcan, terazol, intraconazole, mycostatin, boric acid, tioconazole, undecylenic acid, tolnaftate, imidazole, luliconazole, tavaborole, allylamine, amorolfine, oxiconazole, gluconazole, ciclotirox, naftifine, amphotericin B, sulconazole, butenafine, sertaconazole, efinacanazole, a derivative or prodrug thereof, and combinations thereof.

10. The dimethicone-based delivery composition of claim 1, wherein the dimethicone-based delivery composition further comprises *Aloe vera*.

11. The dimethicone-based delivery composition of claim 1, wherein the active agent is a topical anesthetic.

12. The dimethicone-based delivery composition of claim 11, wherein the topical anesthetic is selected from the group consisting of: benzocaine, butamben, tetracaine, benzyl alcohol, capsaicin, dibucaine, diclofenac, dyclonine, ethyl chloride, hexylresorcinol, lidocaine, prilocaine, methyl salicylate, menthol, pramoxine, proparacaine, trolamine, and combinations thereof.

13. The dimethicone-based delivery composition of claim 1, wherein the active agent is a skin care material, and wherein the skin care material is selected from the group consisting of: chitosan, sulfadiazine, silver sulfadiazine, silver nitrate, silver nanoparticles, and combinations thereof.

14. The dimethicone-based delivery composition of claim 1, wherein the active agent is a wound healing composition selected from the group consisting of: bacitracin, neomycin, polymyxin B, epidermal growth factor, triamcinolone, and combinations thereof.

15. The dimethicone-based delivery composition of claim 1, wherein the active agent is a hemostatic agent selected from the group consisting of: tranexamic acid, chitosan, human fibrinogen, human thrombin, nonhuman fibrinogen, nonhuman thrombin, synthetic fibrinogen, synthetic thrombin, keratin, and combinations thereof.

16. The dimethicone-based delivery composition of claim 1, wherein the active agent is a ferric subsulfate material or Monsel's solution.

17. The dimethicone-based delivery composition of claim 1, wherein the active agent is an acne treating agent selected from the group consisting of: benzoyl peroxide, azelaic acid, salicylic acid, corticosteroids, retinoids, antibiotics, and combinations thereof.

18. The dimethicone-based delivery composition of claim 1, wherein the active agent is a hemorrhoid treating agent selected from the group consisting of: phenylephrine hydrochloride, pramoxine HCL, a corticosteroid, and combinations thereof.

19. The dimethicone-based delivery composition of claim 1, wherein the active agent is a cannabinoid.

20. The dimethicone-based delivery composition of claim 1, wherein the active agent is an anti-inflammatory agent, and wherein said anti-inflammatory agent is selected from the group consisting of: diphenhydramine, corticosteroids, and combinations thereof.

21. The dimethicone-based delivery composition of claim 1, further comprising an excipient, wherein said excipient is selected from the group consisting of: a moisturizer, flavor, pigment, essential oils, zinc oxide, a wetting agent, and combinations thereof.

22. The dimethicone-based delivery composition of claim 1, further comprising an excipient selected from the group consisting of: an oil, a fat, a wax, and combinations thereof.

* * * * *